United States Patent
Mentkow et al.

(10) Patent No.: US 8,409,629 B2
(45) Date of Patent: *Apr. 2, 2013

(54) HEMOSTATIC AGENT COMPOSITION AND METHOD OF DELIVERY

(76) Inventors: Jack Mentkow, Wellington, FL (US); Lisa Mentkow, Wellington, FL (US)

( * ) Notice: Subject to any disclaimer, the term of this patent is extended or adjusted under 35 U.S.C. 154(b) by 1108 days.

This patent is subject to a terminal disclaimer.

(21) Appl. No.: 12/191,323

(22) Filed: Aug. 14, 2008

(65) Prior Publication Data

US 2008/0299226 A1 Dec. 4, 2008

Related U.S. Application Data

(63) Continuation-in-part of application No. 11/453,524, filed on Jun. 15, 2006.

(60) Provisional application No. 60/757,459, filed on Jan. 9, 2006, provisional application No. 60/694,955, filed on Aug. 16, 2007.

(51) Int. Cl.
*A61K 33/12* (2006.01)
*A61K 33/06* (2006.01)

(52) U.S. Cl. ........................ 424/683; 424/684

(58) Field of Classification Search .................. 424/474, 424/683, 684
See application file for complete search history.

(56) References Cited

U.S. PATENT DOCUMENTS

| | | | | |
|---|---|---|---|---|
| 4,748,978 A * | 6/1988 | Kamp | ............................ | 424/445 |
| 5,000,115 A * | 3/1991 | Hughes | ......................... | 119/173 |
| 6,288,076 B1 * | 9/2001 | Kostyniak et al. | ............ | 514/299 |
| 2003/0133990 A1 * | 7/2003 | Hursey et al. | ................. | 424/601 |
| 2004/0028709 A1 * | 2/2004 | Dueva et al. | .................. | 424/401 |
| 2004/0067247 A1 * | 4/2004 | De Sloovere et al. | ........ | 424/409 |
| 2005/0074505 A1 * | 4/2005 | Hursey | .......................... | 424/682 |
| 2005/0266081 A1 * | 12/2005 | Rogozinski | ................... | 424/484 |
| 2006/0015235 A1 | 1/2006 | Ringger et al. | | |
| 2006/0155235 A1 * | 7/2006 | Sawyer | .......................... | 602/48 |
| 2007/0160638 A1 | 7/2007 | Mentkow et al. | | |

FOREIGN PATENT DOCUMENTS

WO 2006088912 A2 8/2006
WO 2007081760 A2 7/2007

OTHER PUBLICATIONS

USGS (US Geological Survey, Smectite Group [Downloaded Sep. 29, 2011] [Retrieved from internet <URL: http://pubs.usgs.gov/of/2001/of01-041/htmldocs/clays/smc.htm >]), (2 pages).*
Elementis (Elementis Specialties, Bentone® EW, (Oct. 2006) [Downloaded Sep. 30, 2011] [Retrieved from internet <URL: http://elementis-specialties.com/esweb/webproducts.nsf/allbydocid/AD7ABD2C D4612AE9852575FF004F387A/$FILE/BENTONE%20EW.pdf >]) (2 pages).*
Thesaurus.com, Inert [Obtained Sep. 30, 2011] [Retrieved from internet <URL: http://thesaurus.com/browse/inert >] (0 pages).*
Carrado et al. (A study of organo-hectorite clay crystallization, Clay Minerals (1997) 32: 29—40 [Downloaded Jul. 26, 2012] [Retrieved from internet <URL: http://www.minersoc.org/pages/Archive-CM/Volume_32/32-1-29.pdf >]), 12 pages.*
Baker et al. (Controlling Bioprocesses with Inorganic Surfaces: Layered Clay Hemostatic Agents, Chem. Mater. (2007) 19:4390-4392), 3 pages.*

(Continued)

*Primary Examiner* — Jason M Sims
*Assistant Examiner* — Miriam A Levin
(74) *Attorney, Agent, or Firm* — Laurence A. Greenberg; Werner H. Stemer; Ralph E. Locher

(57) ABSTRACT

A hemostatic agent composition that includes a clay hemostatic agent which is inert and non-reactive relative to blood clotting proteins and platelets, yet is capable of accelerating the formation of a stable clot when applied to an actively bleeding wound.

25 Claims, 3 Drawing Sheets

OTHER PUBLICATIONS

The Mineral Mine, Hectorite ([Downloaded Jul. 17, 2011] [Retrieved from internet <URL: http://www.mine-engineer.com/mining/mineral/hector.htm >]), 2 pages.*

Wikipedia, Hectorite ([Downloaded Jul. 17, 2011] [Retrieved from internet <URL: http://en.wikipedia.org/wiki/Hectorite >]), 2 pages.*

Galleries, Clinoptilolite ([Downloaded Jul. 17, 2011] [Retrieved from internet <URL: http://galleries.com/minerals/silicate/clinopti/cliniopti.htm >]), 3 pages.*

International Search Report and Written Opinion dated Feb. 24, 2009.

Elementis Specialties, "Additives for Construction Systems"—Tile Adhesives—Rendering/Plasters/Stucos—Eifs—Gypsum Flooring—Bitumious and Asphalt Systems, 2004, 16 pages.

Lordan et al., "Cytotoxic effects induced by unmodified and organically modified nanoclays in the human hepatic HepG2 cell line" Research Article, Journal of Applied Toxicology 2011, 31, published online in Wiley Online Library: Jul. 30, 2010, pp. 27-35.

* cited by examiner

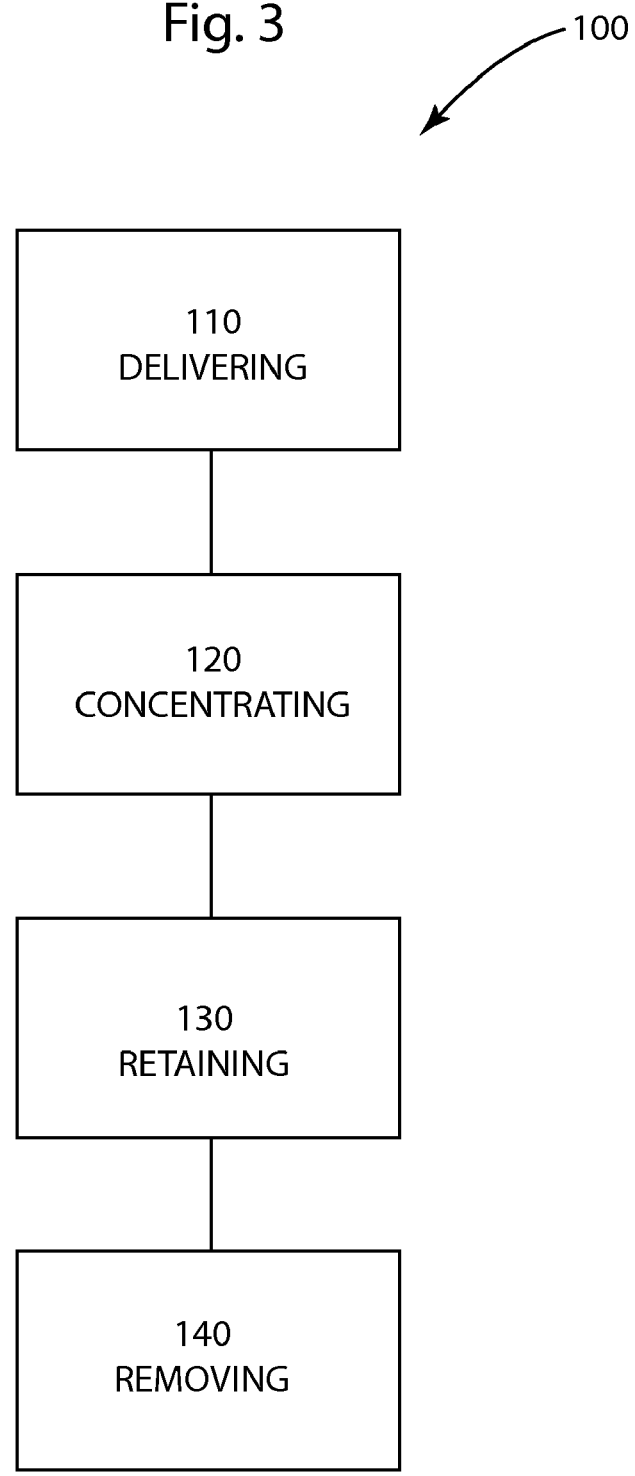

HEMOSTATIC AGENT COMPOSITION AND METHOD OF DELIVERY

INDEX TO RELATED APPLICATIONS

The present application is a Continuation-In-Part of U.S. patent application Ser. No. 11/453,524, filed Jun. 15, 2006 which is based on and for which a claim for priority is made under 35 U.S.C. Section 119(e) to U.S. Provisional Patent Application No. 60/757,459, filed Jan. 9, 2006, and this application also claims the priority under 35 U.S.C. Section 119(e) of U.S. Provisional Patent Application No. 60/964,955, filed Aug. 16, 2007, the disclosures of which are incorporated herein by reference in their entirety.

BACKGROUND OF THE INVENTION

1. Field of the Invention

The present invention is directed to a hemostatic agent delivery composition and system. The composition comprises a hectorite clay and an acceptable carrier composition. One delivery system comprises a delivery assembly having a pouch or receptacle containing a hemostatic agent, the pouch being at least partially defined by a support member in combination with an overlying release member made of a soluble material. More in particular, the hemostatic agent delivery system is structured such that a hemostatic agent is delivered directly to a source of bleeding, and wherein the hemostatic agent is concentrated and retained at the bleeding source to facilitate clotting and terminate hemorrhaging.

Another delivery system comprises a syringe or ejection device containing the composition. The composition may be applied from the syringe directly to a wound site, or may be directed by a catheter, tubing and the like into or near a hemorrhage site.

2. Description of the Related Art

It has long been known that injuries which result in excessive bleeding if not quickly or properly addressed can often prove fatal. Unfortunately, this fact is well supported by data gathered during numerous armed conflicts throughout time. For instance, it has been reported that over 2,500 soldiers died from extremity wounds during the Vietnam War solely because they bled to death. Military data also indicate that approximately 50% of combat casualties die from bleeding, and that the majority die within thirty minutes of the injury. It has also been reported that of the fifty %, approximately sixty % die within the first five minutes while the remaining persons die within one hour if not properly treated.

In addition, it has been estimated that there are over seventy million emergency room visits each year for bleeding. As above, with respect to injuries sustained during battle, bleeding or acute hemorrhaging is a leading cause of death in trauma cases among the civilian population.

As such, it is clear that rapid and effective control of hemorrhaging saves lives. Attempts to address the need for such rapid and effective hemorrhage control have resulted in a development of a number of so called hemostatic bandages and other products purported to facilitate rapid control of bleeding.

One such product comprises a granular zeolite material which may be obtained from volcanic lava rocks. This material is placed into a bleeding wound where it absorbs water molecules from the blood, thereby creating a high platelet concentration which promotes clotting. However, it has been documented that the absorption process affected by this zeolite is a highly exothermic reaction which generates a considerable amount of heat, attributable to reaction with the iron content of the zeolite. More specifically, temperatures ranging from 90° C. to 100° C. have been reported following use of the material, causing second degree burns to soldiers injured and treated with this product in Iraq, as well as to those persons administering the product, even though personnel administering this product must be trained and certified to administer the same.

A further drawback to this product is that the zeolite material is packaged to be simply poured on to an open wound, however, in the case of hemorrhaging of any significance, such as may occur due to laceration of a major artery, the pressure of blood exiting the wound will simply cause the material to be dispersed thereby minimizing and/or eliminating the effectiveness of the clotting properties therein. Another disadvantage is that the zeolite's efficacy is exhausted at first contact with blood such that a clot may be formed distant to the actual wound source without stopping hemorrhaging. Yet another disadvantage of this product is that the zeolite material is granular in nature, making it difficult to subsequently remove the material from the wound via normal means such as irrigation and/or suctioning of the wound area, once the injured person is transferred to an operating room or other such treatment facility.

Another product is made from chitosan, which is derived from the exoskeletons of shellfish. Reports as to the effectiveness of this device in hemorrhage control are conflicting, in particular, its effectiveness in the event of hypothermia in the patient, such as may occur from shock following significant blood loss, is reported to be severely reduced or diminished. In addition, there have been reports of the device being improperly applied, e.g., the wound is not contacted by the active surface due to the device being placed into the wound site upside down. Since this product is derived from living organisms, it has an extremely limited shelf life during which time it must either be utilized or disposed of, and given the significant cost of each unit, this is a further considerable disadvantage.

Another type of hemostatic bandage is manufactured from single cell algae and comprises poly-N-acetylglucosamine. This device is structured to enable persons with minimal training to quickly and effectively control and/or stop hemorrhaging from extremity trauma. More in particular, when the material comes in contact with blood it reportedly stimulates platelet aggregation and activation which causes the body to secrete tromboxane, which stimulates the blood vessels to constrict in the vicinity of the wound. Stated differently, the poly-N-acetylglucosamine material acts as a catalyst to accelerate the normal clotting process thereby accelerating the bodies own control of the bleeding. Once again, since this product is derived from living organisms, it has a limited shelf life during which it must be utilized or disposed. Further, its effectiveness in the event of hypothermia in the patient, such as in the above example, is questionable.

Another material which is structured to be applied, i.e., poured, directly to wounds has been synthesized from potato starch. Reportedly, the particles accelerate natural clotting by concentrating blood solids forming a gel around the same so as to promote clotting. In particular, the larger particles of the blood components are concentrated on the surface of the synthesized potato starch product, thereby promoting accelerated clotting. As noted, this material is also in a powder form and has been applied directly to a bleeding wound with a bellows type applicator as noted above with respect to the zeolite material, however, in the event of excessive bleeding such as a major artery, the pressure of the blood flowing from the wound is often sufficient to disperse the powder thereby once again, minimizing or eliminating the clotting property exhibited therein, even though the wound site is to be covered with a standard bandage and pressure applied after treatment with the synthesized potato starch material.

Yet another powdered material is composed from a hydrophilic polymer and a potassium salt in combination with a bovine based thrombin material. This powder is also reported to stop bleeding on contact based upon studies for various minor wounds, in which no covering bandage is required, however, as noted above with respect to the other "pour" type products, in the event of any significant bleeding, the blood pressure itself is likely to disperse the product, thereby reducing or eliminating any hemostasis it was intended to effect.

One product patented from TraumaCure (Bethesda, Md.) is a balloon device. A deflated balloon is inserted through the wound entry point and then inflated while in the wound cavity, putting pressure against the wound walls and source of bleeding.

In view of the foregoing, it is clear that it would be a significant benefit to provide a system for rapid, effective, and efficient control of hemorrhaging including hemorrhaging of major arteries, which may be quickly and properly applied by personnel with minimal training. More in particular, it would be beneficial to provide a system for delivering an effective amount of a hemostatic agent directly to a wound site, as well as providing a mechanism to maintain an effective amount of the hemostatic agent at the wound site to control bleeding. Also, it would be advantageous for such a system to comprise a hemostatic agent which is essentially nonreactive and hypoallergenic when applied to a wound. Further, the hemostatic agent employed in such a system should promote clotting of the blood in a non-reactive manner, i.e., without exothermic reaction with the blood and the localized temperature increase associated therewith. Yet another advantage may be realized by providing such a system with a hemostatic agent which is inorganic, thereby benefiting from an essentially indefinite shelf life.

SUMMARY OF THE INVENTION

The present invention is directed to a hemostatic agent composition and delivery systems which are structured to deliver a hemostatic agent composition directly to a hemorrhage site, for example, a lacerated artery, so as to facilitate clotting of the blood and terminate hemorrhaging at the site. As such, the hemostatic agent delivery system of the present invention is further structured to concentrate and retain the hemostatic agent at the hemorrhage site, once again, to facilitate clotting and terminate hemorrhaging.

The composition of the present invention is easily and economically manufactured and priced accordingly, affording the consumer and general public greater access to these life saving inventions.

At least one embodiment of the delivery system of the present invention includes at least one hemostatic agent composition structured to facilitate blood clotting. More in particular, at least one hemostatic agent of the present invention comprises a smectite clay material. In at least one further embodiment, a hectorite clay is utilized as the hemostatic agent. The present invention encompasses the utilization of a clay material as a hemostatic agent either alone or in combination with one or more additives, as is discussed further below.

To facilitate delivery of the hemostatic agent to a hemorrhage site, the delivery system of the present invention further comprises a delivery assembly which is structured to at least temporarily contain an amount of the hemostatic agent, at least until the agent is delivered proximate to a hemorrhage site. The delivery assembly, in at least one embodiment, includes a release member disposed in overlying relation to a support member. More in particular, the release member and the support member are cooperatively structured to at least temporarily contain the hemostatic agent therebetween, the release member and the support member being attached about their respective peripheries.

In order to achieve releasable containment of one or more hemostatic agents via the delivery assembly of the present invention, the release member comprises a soluble material structured to at least partially dissolve and release the hemostatic agent upon disposition directly proximate to a hemorrhage site. In at least one embodiment, the release member comprises a soluble polymeric material, such as, by way of example only, a polyvinyl alcohol material.

To further facilitate delivery of an amount of a hemostatic agent directly to a hemorrhage site, the delivery assembly of the present invention may also include a handle member attached to an outer surface of the support member, wherein the handle member is structured to facilitate handling of the delivery system by a user. At least one embodiment of the present invention includes a handle member having a visual indication to facilitate location or identification of the handle member by a user. This feature may prove critical in the hectic and often chaotic environment in which the hemostatic delivery system of the present invention is utilized, such as, on the battle field, field medical unit, or hospital emergency room.

The present invention further encompasses a method of application of a hemostatic agent to a hemorrhage site including the step of delivery of an amount of a hemostatic agent, wherein the hemostatic agent comprises a beneficiated hectorite clay material, directly proximate the hemorrhage site. The method further includes concentrating the amount of hemostatic agent in a substantially conforming relation to the configuration of the hemorrhage site, and retaining the amount of the hemostatic agent at the hemorrhage site in a substantially occluding relation so as to facilitate clotting and terminate hemorrhaging at the site. The method further provides for removing the hemostatic agent from the hemorrhage site via standard irrigation and suction procedures, once a patient has been stabilized and transferred, for example, to a fixed facility operating room or field operating unit. As noted above, the hemostatic agent of the present invention is structured to form a stable clot such that the patient may be moved, once hemorrhaging has been effected.

These and other objects, features and advantages of the present invention will become more clear when the drawings as well as the detailed descriptions are taken into consideration.

BRIEF DESCRIPTION OF THE DRAWINGS

For a fuller understanding of the nature of the present invention, reference should be had to the following detailed description taken in connection with the accompanying drawings in which:

FIG. 3 is a diagrammatic representation of a method of application of a hemostatic agent in accordance with the present invention.

Like reference numerals refer to like parts throughout the several views of the drawings.

DETAILED DESCRIPTION OF THE PREFERRED EMBODIMENT

Figure 1:
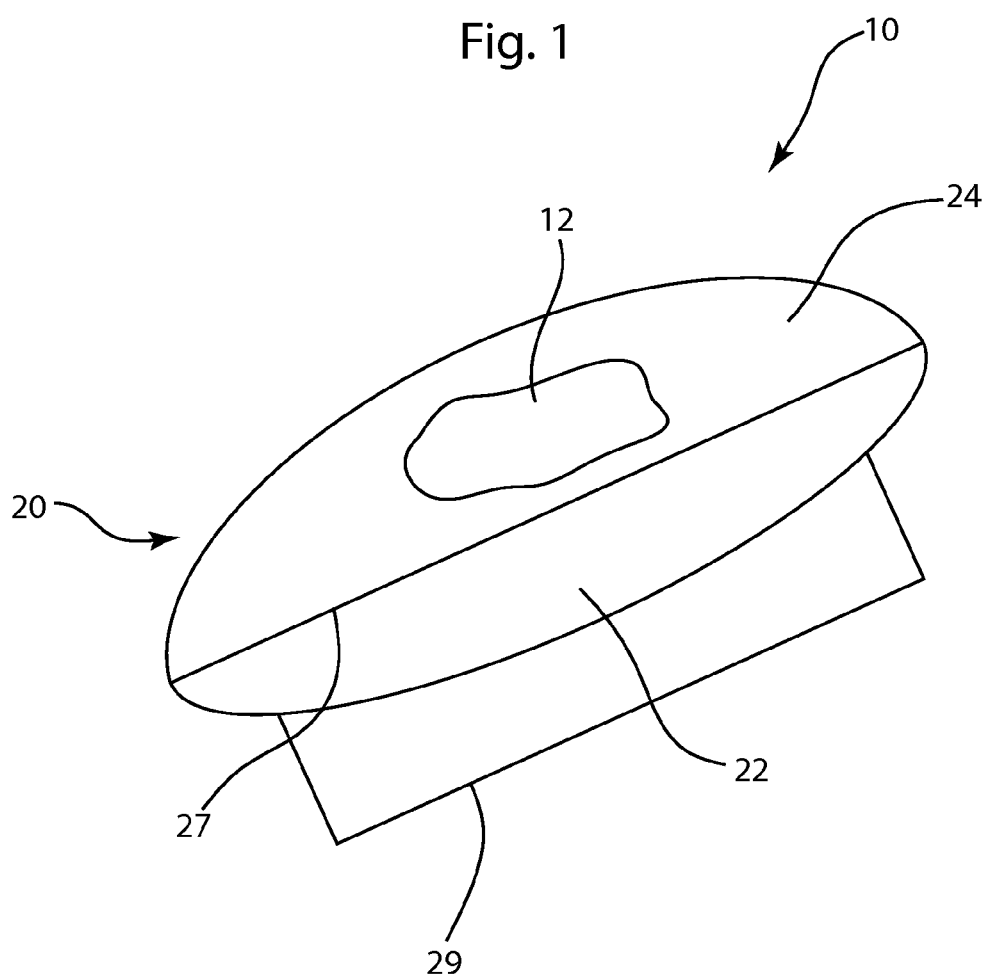
FIG. 1 is a perspective view of one preferred embodiment of a hemostatic agent delivery system in accordance with the present invention.

As previously noted, the present invention is directed to a hemostatic agent delivery system, generally as shown as 10 in the figures, which is structured to facilitate delivery of a hemostatic agent directly proximate a hemorrhage site. More in particular, the present invention is directed towards a hemostatic agent delivery system 10 which may be quickly and effectively utilized to facilitate clotting and to control and/or terminate hemorrhaging of an injured person, such as, a soldier wounded on a battle field, by personnel with minimal training. As will become apparent from the following, the hemostatic agent delivery system 10 of the present invention is structured such that personnel with minimal instruction in its use will be able to readily identify the proper orientation of the delivery assembly 20, so as to facilitate disposition of the delivery assembly 20 directly proximate a hemorrhage site.

To reduce and/or terminate excessive bleeding at a hemorrhage site, the hemostatic agent delivery system 10 of the present invention comprises at least one hemostatic agent 12. Of course, it is within the scope and intent of the present invention to comprise a plurality of hemostatic agents 12, or a combination of one or more hemostatic agent 12 and one or more additives, such as may be desirable to enhance the performance of one or more hemostatic agent 12. As one example, the hemostatic agent 12 of the present invention, in at least one embodiment, comprises a hydroxyethyl cellulous additive structured to enhance the absorption of water from the blood by the hemostatic agent 12, thereby increasing the rate of clot formation, and termination of the hemorrhage. As noted above, bleeding is a major cause of death in both military and civilian injuries, and the present invention enables quick and effective control and/or termination of hemorrhaging, which is proven to save lives.

In at least one embodiment of the present invention, at least one hemostatic agent 12 comprises smectite clay. Smectite is a family of naturally occurring layered swelling clays which include bentonite, also known as montmorillonite, hectorite, and saponite. Kaolinite, a related clay, is less absorbent and swelling than the aforementioned. More in particular, the smectite clays are layered silicates which swell in water, and are widely used as rheological additives. Specifically, the silicate platelets comprise three layers, two silicate dioxide layers which embed a metal oxide layer. In bentonite clays, the metal oxide layer is mainly aluminum, whereas in hectorite clay the metal oxide layer comprises magnesium. The surfaces of both hectorite and bentonite platelets are negatively charged because the divalent magnesium in hectorite is partly replaced by monovalent lithium, which results in a charge deficiency. Similarly, the aluminium in bentonite is partly replaced by magnesium. The negative surface charge is balanced by cations; in the case of some hectorites (e.g. Elementis Specialties' hectorite) these are sodium ions. Bentonites, on the other hand, mainly occur in the calcium form, which reduces the swelling ability of the clay and its rheological efficiency. More importantly, bentonite may include approximately 4% by weight of ferric and ferrous oxides, hectorite clay is essentially iron free, comprising generally less than one-half of one percent (<0.50%) by weight. This is important, as a presence of iron is believed to promote exothermic reactions between hemostatic agents and body fluids during absorption processes. A further benefit of hectorite clay, for use in conjunction with the present invention, is that it can be highly beneficiated, i.e., purified and ground, such that the particle size of hectorite clay is approximately 10% that of similar bentonite clays. One preferred embodiment of the present invention comprises a beneficiated hectorite clay as a hemostatic agent 12. More in particular, the present invention may comprise Bentone EW.RTM. which is a highly beneficiated hectorite clay available from Elementis Specialties of Hightstown N.J. Bentone EW.RTM. has a density of about 2.5 grams per cubic centimeters (g/cm.sup.3) and, more importantly, a particle size distribution wherein approximately 94% or greater of the material is less than 200 mesh screen size.

Of course, as noted above, the present invention comprises a hemostatic agent delivery system 10 comprising a plurality of hemostatic agents 12, as one example, at least one embodiment may comprise bentonite clay, or a combination of hectorite and bentonite clays in a variety of proportions. Also as noted above, one or more additives may be combined with the hemostatic agent 12 to enhance the hemostatic properties thereof. As just one example, in one further preferred embodiment of the present invention the hemostatic agent 12 comprises a highly beneficiated hectorite clay in combination with a hydroxyethyl cellulous additives. More in particular, the hemostatic agent 12 of one preferred embodiment comprises Bentone LT.RTM. once again, available from Elementis Specialties.

An important consideration for selection of the hemostatic agent 12 for use in the present invention is that the agent 12 be essentially inert and non-reactive when disposed in contact with in open wound, and the blood or other body fluids being released therefrom. More in particular, as noted above, the hectorite clays do not include iron components to any significant degree therefore they are essentially non exothermic upon contact with water, blood, or other aqueous or bodily fluids. In addition, because of the powdered physical configuration of beneficiated hectorite clay, it serves to aid in the formation of a stable clot upon application to a hemorrhage site. Specifically, Bentone EW.RTM. is purified and pulverized into a fine powder in the beneficiating process thereby increasing the effective surface area of the material, and resulting in an increase in absorptive capacity for removing the water content of blood so as to concentrate the blood platelets to facilitate clotting and to form a stable clot at the hemorrhage site. In tests conducted on swine, stable clots were formed at a hemorrhage site consisting of a lacerated femoral artery utilizing the hemostatic agent delivery system 10 and hemostatic agent 12 in accordance with the present invention.

The hemostatic delivery system 10 of the present invention further comprises a delivery assembly 20 which is structured to facilitate disposition of an amount of a hemostatic agent 12 directly proximate a hemorrhage site. More in particular, the delivery assembly is structured to releasably contain an amount of the hemostatic agent 12 for delivery to a hemorrhage site. In one preferred embodiment, the delivery assembly 20 includes a release member 24 which is disposed in overlying relation to an oppositely disposed support member 22, the release member being attached to and about a periphery of the support member 22. More in particular, the release member 24 and the support member 22 are cooperatively structured so as to at least temporarily contain the amount of hemostatic agent 12 for delivery to a hemorrhage site, as illustrated in FIG. 1.

In at least one embodiment, the support member 22 comprises a sterile dressing, such as, by way of example, an anti-stick gauze pad. It will be appreciated, given the nature of the present invention, that each of the components comprising the delivery system 10 will be sterilized and packaged utilizing appropriate procedures to assure that a hemorrhage site is not exposed to external contamination. It will be further appreciated, that a support member 22 comprising a sterile gauze pad will facilitate conforming the hemostatic agent delivery system 10 of the present invention substantially about the configuration of a wound so as to occlude the wound to facilitate the reduction and termination of hemorrhaging therefrom.

Looking next to the release member 24 of the present invention, the release member 24 comprises a soluble material of construction which is structured to at least partially dissolve upon contact with an aqueous solution, such as blood discharging from a wound. Upon dissolving, the release member 24 of the present invention will release the amount of hemostatic agent 12 from the delivery assembly 20 directly proximate to the hemorrhage site in a rapid and effective manner. In at least one embodiment, the delivery assembly 20 of the present invention comprises a release member 22 constructed of the soluble polymeric material which is structured to dissolve in blood and body fluids therewith.

In one preferred embodiment, the release member 22 comprises a polyvinyl alcohol material which will substantially dissolve upon contact with blood at a hemorrhage site. The polyvinyl alcohol material of the release member 22 may be constructed of any of a variety of thicknesses, thereby controlling the rate at which the release member 22 will dissolve and, as such, the rate at which the hemostatic agent 12 will be delivered to a hemorrhage site, a factor which is also affected by the volume of fluid present. As such, the hemostatic agent delivery system 10 of the present invention may be customized for application to a variety of wounds of varying degrees of severity.

As one example, the hemostatic agent 12 may be applied directly proximate a superficial wound, in which case, the release member 22 will preferably comprise a very thin material so as to permit rapid dissolution and release of the hemostatic agent 12. For more severe hemorrhages, for example, laceration of a major artery, the release member 22 will comprise a greater thickness, to assure that the hemostatic agent delivery system 10 may be disposed proximate the hemorrhage site and configured to substantially conform to the wound prior to dissolution of the release member 24 and subsequent release of the hemostatic agent 12 to the hemorrhage site.

To facilitate attachment of the release member 24 to the support member 22, the delivery assembly 20 of the present invention further comprises a seal mechanism 27 structured to facilitate attachment between the members. More in particular, the seal mechanism 27 of the present invention comprises at least one seal member 28 which is structured to hermetically seal the release member 24 to the support member 22. In at least one embodiment of the present invention, the seal member 28 comprises a heat reactive adhesive. In one further embodiment, the seal member 28 comprises an iron-on adhesive. Of significance is that the seal member 28 of this embodiment is structured to bond two dissimilar materials, each of which independently are structured to be non-adhesive, thereby forming a hermetically sealed pouch 21 which releasably contains one or more hemostatic agent 12.

Figure 2:
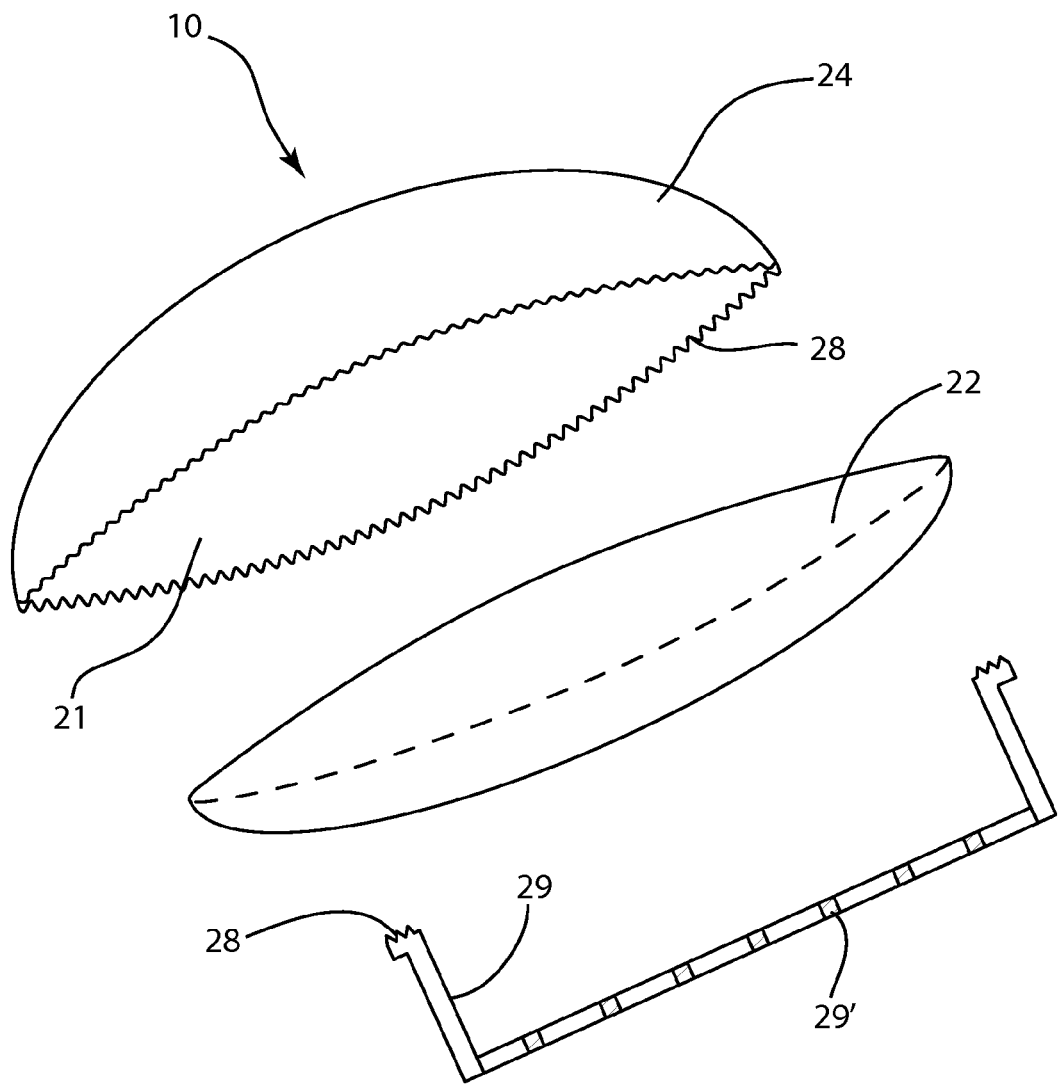
FIG. 2 is a partially exploded view of the embodiment of FIG. 1.

In at least one embodiment, the delivery assembly 20 of the present invention further comprises a handle member 29, as illustrated in the figures. The handle member 29, serves several purposes, the first of which being to facilitate disposition of the delivery assembly 20 directly proximate to a hemorrhage site to facilitate delivery of a hemostatic agent thereto. More in particular, the handle member 29 is structured and configured to be grasped by one hand of a user and allow the user to quickly and effectively direct the surface of the delivery assembly 20 comprising the release member 24 directly onto a hemorrhage site, such as, a lacerated artery. As seen in FIGS. 1 and 2, the handle member 29 is attached to an outer face of support member 22 and disposed opposite the outer surface of the release member 24, and as such, the handle member 29 allows for the user to grasp the delivery assembly 20 with hands that may be wet or bloody, yet hindering contact with the release member 24, so as to prevent inadvertent and premature release of the hemostatic agent 12.

In at least one embodiment, the handle member comprises a visual indication 29, to facilitate location of the handle member 29 by a user. More in particular, the visual indication 29' may include indicia such as letters, symbols, stripes, etc., applied directly onto the handle member 29 as shown in FIG. 2. In at least one embodiment, the visual indication 29' may comprise a color contrast between the support member 22, typically being a white color sterile gauze pad, and the handle member 29, which may comprise a bright color or color pattern, for example, a striped pattern as illustrated in FIG. 2.

As indicated above, the present invention further comprises a method for application of a hemostatic agent to a hemorrhage site, generally as illustrated at 100 in FIG. 3. More in particular, the method 100 of the present invention comprises delivering 110 an amount of a hemostatic agent comprising a beneficiated hectorite directly proximate a hemorrhage site. The method 100 further comprises concentrating 120 the amount of the hemostatic agent in a substantially conforming relation to the configuration of the hemorrhage site, and retaining 130 the amount of the hemostatic agent at the hemorrhage site in a substantially occluding relation to the hemorrhage site so as to facilitate clotting and terminate hemorrhaging therefrom. In at least one embodiment, the method 100 of the present invention further comprises the step of removing 140 the amount of the hemostatic agent from the hemorrhage site via irrigation and suction, once a patient is stabilized, for example, upon transference to a field hospital or an emergency room.

Further contemplated in the present invention is a composition that is delivered to a wound that has the ability to assist in blood clotting both in the wound where the composition is applied, and will travel in the body or wound track to assist in the clotting of other wounds.

Formulations

The table below provides information on formulation development. The first column is a number identifying the formulation. A legend appears after the chart that details the components used in the various formulations.

| | Gm. Measure by Weight | | | | | | | | Oz. Measure by Weight | | | | |
|---|---|---|---|---|---|---|---|---|---|---|---|---|---|
| | C-25 | C-18 | TEA | H2O | XG | Carag | CG | HEC | Glyc | PPG | EW | Glyc | H2O | LT |
| 1 | 4.5 | | 4.5 | | | | | | | 4 | 2 | | | |
| 2 | 9 | | 9 | 9 | | | | | | 4 | 2 | | | |
| 3 | | 9 | 9 | | | | | | | 5 | 2 | | | |

-continued

| | Gm. Measure by Weight | | | | | | | | | Oz. Measure by Weight | | | | |
|---|---|---|---|---|---|---|---|---|---|---|---|---|---|---|
| | C-25 | C-18 | TEA | H2O | XG | Carag | CG | HEC | Glyc | PPG | EW | Glyc | H2O | LT |
| 4 | 4.5 | | 4.5 | 9 | | | | | | 4 | 2 | | | |
| 5 | 9 | | 9 | | | | | | | 4 | 2 | | | |
| 6 | | 4.5 | 4.5 | | | | | | | 4 | 2 | | | |
| 7 | | 4.5 | 4.5 | 9 | | | | | | 4 | 2 | | | |
| 8 | 9 | | 9 | | | | | | | 5 | 2 | | | |
| 9 | | | | | 9 | | | | | 4 | 2 | | | |
| 10 | | | | | | | 9 | | | 4 | 2 | | | |
| 11 | | | | | | 9 | | | | 4 | 2 | | | |
| 12 | | | | | | | | 9 | | 4 | 2 | | | |
| 13 | | | | | | | 9 | | | 3 | 2 | 2 | | |
| 14 | | | | | | 9 | | | | 3 | 2 | 1 | | |
| 15 | | | | | | 9 | | | | 3.5 | 2 | 0.5 | | |
| 16 | | | | | | 18 | | | 9 | 4 | 2 | | | |
| 17 | | | | | 9 | | 9 | | | 3 | 2 | 1 | | |
| 18 | | | | | 9 | | 9 | | | 4 | 2 | | | |
| 19 | | | | | 9 | | | | | 4 | 2 | | 0.25 | |
| 20 | | | | | 4.5 | | | | | 4 | 2 | | 0.25 | |
| 21 | | | | | 2.25 | | | | | 4 | 2 | | 0.25 | |
| 22 | | | | | 1.125 | | | | | 4 | 2 | | 0.25 | |
| 23 | | 14.4 | 14.4 | | | | | | | 3 | 2 | | 1 | |
| 24 | 9 | 9 | | | | | | | | 4 | 2 | | 1 | |
| 25 | | | 14.4 | 14.4 | | | | | | 2 | 2 | | 2 | |
| 26 | | 14.4 | 14.4 | | | | | | | 5 | 2 | | 0.5 | |
| 27 | | | | | 1.8 | | | | | 3.5 | 2 | | 0.5 | |
| 28 | | | | | 0.9 | | | | | 3.75 | 2 | | 0.25 | |
| 29 | | | | | 1.8 | | | | | 4 | 2 | | 0.5 | |
| 30 | | | | | 2.7 | | | | | 5 | 2 | | 0.5 | |
| 31 | | | | | 2.7 | | | | | 4 | 2 | | 0.5 | |
| 32 | | | | | | 2.7 | | | | 4 | 2 | | 0.5 | |
| 33 | | | | | | | 2.7 | | | 4 | 2 | | 0.5 | |
| 34 | | | | | | | | 2.7 | | 3 | 2 | | 0.5 | |
| 35 | | | | | 2.7 | | | | | 4.5 | 2 | | 0.5 | |
| 36 | | | | | 7.2 | | | | | 4.5 | 2 | | 0.6 | |
| 37 | | | | | 7.2 | | | | | 4 | 2 | | 0.6 | |
| 38 | | | | | | | | | | 4 | | | 2 | |
| 39 | | | | | | | | | | 4 | 1.8 | | 0.2 | |
| 40 | | | | | | | | | | 4 | 1.9 | | 0.1 | |
| 41 | | | | | | | | | | 4.2 | 1.9 | | 0.1 | |
| 42 | | | | | | | | | | 4 | 1.95 | | 0.05 | |
| 43 | | | | | | | | | | 4 | 2 | | 0.025 | |
| 44 | | | | | | | | | | 4.5 | 2 | | 0.025 | |
| 45 | | | | | | | | | | 4.5 | 1.9 | | 0.1 | |
| 46 | | | | | | | | | | 4.2 | 1.9 | | 0.1 | |
| 47 | | | | | | | | | | 4.5 | 1.8 | | 0.2 | |
| 48 | 9 | | 9 | 18 | | | | | | 4 | 2 | | | |

Legend:
C-25 = Carbomer25 (Carbopol ® Aqua SF-1)
C18 = Carbomer18
TEA = Triethanolamine
XG = Xanthan Gum, TIC
Carag = Carrageenan
CG = Cellulose Gum
HEC = Hydroxyethyl Cellulose
Glyc = Glycerin
PPG = Propylene Glycol
EW = Bentone EW (Hectorite Clay)
LT = Bentone LT (Hectorite Clay + Hydroxyethyl Cellulose 50%/50% mixture)
PolySorb = Polysorbate 80

Table 2

Table 2 represents an evaluation of each formulation number in terms of relative consistency and separation stability.

TABLE 2

| | Ideal = 3 Consistency | Ideal = 5 Separation Stability | Notes |
|---|---|---|---|
| 1 | 3 | 3 | |
| 2 | 5 | 4 | |
| 3 | 3 | 3 | 2 |
| 4 | 4 | 5 | 4 |
| 5 | 5 | 5 | 5 |
| 6 | 6 | 3 | 3 |
| 7 | 3 | 3 | |
| 8 | 5+ | | 1 |

TABLE 2-continued

| | Ideal = 3 Consistency | Ideal = 5 Separation Stability | Notes |
|---|---|---|---|
| 9 | 4 | 4 | |
| 10 | 3 | 2 | |
| 11 | 3 | 4 | |
| 12 | 3+ | 4 | |
| 13 | 3 | 4 | |
| 14 | too thick | unstable | |
| 15 | too thick | unstable | |
| 16 | too thick | unstable | |
| 17 | too thick | | |
| 18 | too thick | | |
| 19 | too thick | | |
| 20 | too thick | | |
| 21 | 4 | | |
| 22 | 3 | 2-3 | |
| 23 | too thick | | |
| 24 | 3 | 2-3 | |
| 25 | too thick | | |
| 26 | 3 | 3+ | |
| 27 | 5+ | NA | |
| 28 | 5 | NA | |
| 29 | 3 | 4 | Separates after 1 day @room temp, No separation 3 days @150° F. |
| 30 | 3 | 3 | 3 Days @room temp, 3 Days @150° F. |
| 31 | 4 | 4 | 3 Days @room temp, 3 Days @150° F. |
| 32 | 3+ | | Separates after 3 Hrs @room temp. |
| 33 | 3 | 3 | Separates after 3 Days @room temp |
| 34 | 5 | NA | |
| 35 | 3 | 4 | 2 Days @room temp, 3 Days @150° F. |
| 36 | 3− | 3 | 2 Days @150° F., slightly looser than #11 formula |
| 37 | | 3 | 2 Days @150° F. |
| 38 | too thick | 4+ | |
| 39 | 5+ | 5 | |
| 40 | 5 | 5 | Heated |
| 41 | 5 | 5 | Heated |
| 42 | 5 | 3 | Heated |
| 43 | 5 | 3 | |
| 44 | 3 | 2 | |
| 45 | 2 | 2-3 | |
| 46 | 3 | 5 | No absorption |
| 47 | 3 | 3 | Minimal absorption |
| 48 | 3 | 5 | |

Legend Scale:
Consistency = ease of flowability of formula through syringe and product cohesiveness
Consistency Scale = Loose to Stiff (1-5), Ideal = 3
Separation Stability = whether formula in syringe separated after 3 days @room temp and/or 3 days@150° F.
Separation Stability Scale = Failure to None (1-5), Ideal = 5

Formulation 48—Final Formulation—Tested 3× Freeze/Thaw cycle, and 3×150° F., 3 months@~75° F., no separation. Tested absorption rate. Observed excellent absorption with more than eight times liquid volume absorption in <1 minute.

The composition demonstrated stability from 32° F.-150° F.

A composition based on formulation 48 was tested as set forth below.

The composition was tested and found to exhibit the following characteristics:

Adhesion Strength

A small amount of a composition of formula 48 was tested for a determination of the adhesive strength of the product at four coating thicknesses. A small spring type tensiometer (Hunter Spring brand) was connected to small wooden blocks having two smooth surfaces (each 2.25 sq.in) to be coated with the composition. The test would determine the pull strength (psi) required to cause the composition to fail.

SUMMARY OF ADHESION TEST DATA FOR MEDICAL PASTE

| Coating Test No. | Adhesion* Thickness | (psi) |
|---|---|---|
| 1 | <15 mil (0.015 in.) | 1.078 |
| 2 | 1/32 in. (0.0312 in.) | 0.542 |
| 2 | 1/16 in. (0.0625 in) | 0.258 |
| 4 | 1/8 in. (0.125 in.) | 0.230 |

(1) The hemostatic composition shows good adhesion (greater than 1 pound per square inch) for very thin coatings between two wooden test surfaces.
(2) For a coating thickness of 1/32 inch the adhesion drops to 0.542 psi.
(3) For a coating of 1/16 inch or greater, the adhesion drops further.

Viscosity

A composition according to formula 48 tested kinematic viscosity at room temperature (25° C.) using a Brookfield Viscometer, Model No. RVF.

Results

Kinematic Viscosity: 356,000 cps
(Spindle 7, at 4 RPM)
cps=Centipoises

Test Methods and Results

Test 1

The intention for the first application was to apply the product to a femoral bleed caused by a puncture type wound with a small skin opening in a swine to simulate a stabbing or shrapnel type of injury. An incision on the skin of approximately 2 cm in length was made. A scalpel was inserted through the skin where a strong venus flow was achieved. One 60 cc syringe full of the hemostatic agent composition was applied to the wound and it was able to stop the bleeding within 3 minutes.

Test 2

The second test was performed on a ballistic wound track from a shotgun discharge. The subject in particular had already received a wound to the outside of the rump which had torn the skin open with some underlying tissue damage from a previous wounding phase. The wound created for the test of the product was a shotgun blast using a special round which is commonly used by SWAT teams to blast the locks of doors to gain entry into buildings. The shotgun was placed approximately six inches away from the skin. The blast left a hole about the size of a nickel with burn marks around the wound entrance. After about 5 seconds the blood began to appear at the site of the wound. Two 60 cc syringes of the hemostatic composition were applied inside the wound track and direct pressure was applied over the wound. After 5 minutes of direct pressure the bleeding was under control. After about half an hour the wound was examined to visualize the damage of the shotgun blast and the efficacy of the product. Using a scalpel an incision was made across the entry wound of the blast until a wound track that went all the way through to the other side of the leg was located. The product had properly filled and followed the wound track to the other side.

Test 3

Purpose of Study: Examine the efficacy of the hemostatic agent composition after inducement of a lethal groin injury by shotgun ammunition.

Methods: A trial examination of a (non-approved FDA) hemostatic agent composition was applied following a complex groin injury to the femoral vessels in an animal model that simulates combat injury. This trial examination adhered to the policies and principles as stated in the Guide for the Care and Use of Laboratory Animals (Institute of Laboratory Animals Resources, National Research Council, National Academy Press, 1996) and the methods used in this trial were approved by an independent Intuitional Animal Care and Use Committee (IACUC), 2007.

One Yorkshire swine (~82 kg) was anesthetized with an intramuscular Telazol (ketamine and valium 30 mg/kg). An endotracheal tube was inserted in addition to an IV line placed in a left external jugular vein using a surgical cut down technique. Patency of the IV line was maintained with an initial saline bolus flush. The IV saline was frequently flushed following IV drug administration. The veterinary staff monitored the animal to maintain sedation along with pain management throughout the 180 minutes.

Once positioned on an authorized weapons range the right proximal medial thigh was manually exposed and a black marker pen was used to place an X on the skin at the desired point of injury. A lethal injury was induced by a 12-gauge shotgun slug fired 6-8 inches from the black X mark. This traditional shotgun slug (1500-1700 fps) induced femoral artery and vein disruption causing uncontrolled hemorrhage inside the wound cavity with evidence of an entry and exit wound. Severe bleeding was observed by the investigators immediately after slug penetration. Time was recorded at point of injury. A gloved hand technician applied manual compression equal to ~150 mmHg; (Arnuad et al 2007) over the entry wound. Within 20-30 seconds, manual pressure was released and the wound cavity was filled with gauze and manual pressure was reapplied for one minute in effort to gain hemorrhage control before the hemostatic agent was applied. Without good hemorrhage control prior to hemostatic agents is administered, a high percentage of agent failure is observed after 5 minute of manual pressure (J. Hagmann personal communication). At the end of this period, manual pressure was released, gauze was completely removed and a single 60 cc syringe containing the hemostatic agent within a suspension solution was injected into the wound cavity in less than 5 seconds. This was followed by gauze wound packing placed on top of the agent administration site to ensure equal distribution of this agent down to the disrupted femoral vessels. Manual pressure (~150 mmHg) was then immediately applied directly over the wound site for a total of five minutes without interruption. Immediately of this period manual pressure was released slowly and the wound was observed for bleeding. Since no obvious bleeding occurred after 2 minutes, the top layers the gauze was removed down to the hemostatic agent material and we continued to observed for bleeding. No partial or massive bleeding occurred over the next 10 minutes. Within 10 minutes, it was decided to repeat this injury on the left proximal medial thigh. Two 12-gauge shotgun slugs were fired into the femoral vessel region within seconds since the first slug did not cause immediate massive hemorrhage. The same methods listed above were followed. At no time was there any bleeding from this second wound cavity or even from the first wound cavity.

The swine was lifted back on an army litter and carried 200 yards down a slight uneven grade back to the training area without rebleeding and placed under a tent where the animal was covered with an impermeable plastic wrap to prevent heat loss and was monitored for approximately additional 120 minutes. Vital signs (HR, RR, SpO2, rectal temp) were continuously recorded every thirty minutes from point of injury along with all drug administered by the veterinary staff. At no time in this prolonged care phase did either wound site continue to bleed.

Summary: After 180 minutes from the point of injury, the hemostatic agent application into these two wound cavities followed by manual pressure arrested lethal arterial and venous hemorrhage within 5 minutes. It is most evident that the agent has unique hemostatic characteristics that have been successfully demonstrated to be efficacious to arrest arterial hemorrhage induced by a 12-gauge slug mechanism of injury. The method to deliver this agent, as a solution applied from a single or multiple 60 cc syringes, is very unique and has potentially great application of treating specific combat injuries creating a wound track.

EXAMPLES

In one embodiment, the formulation comprises:

| | |
|---|---|
| Propylene Glycol (PPG) | 55.56% |
| Hectorite | 27.78% |
| H2O | 8.34% |
| Carbomer (Carbopol ® Aqua SF-1)) | 4.17% |
| Triethanolamine (TEA) | 4.17% |

The composition is prepared by:
1. Mixing Carbomer and H2O
2. Add in TEA and mix
3. Add PPG and mix
4. Add hectorite and mix The resulting mixture has a viscosity of more than 50,000 CPs. The pH of the composition is 7.68 and the specific gravity is 1.2773. This specific gravity has the added benefit of preventing dispersion of the mixture even against major arterial bleeding.

A preferred hectorite has a particle size of 95% less than 0.076 mm (less than 76 µm, or 76 microns).

An advantage of the present invention is the composition does not interfere with the chemical-physiological processes of the coagulation process. That is to say, the chemical, physical, and physiological processes of both intrinsic and extrinsic blood coagulation mechanism are not affected by the hemostatic composition of the present invention.

One mechanism that has been observed is the composition absorbs up to eight times its weight of water in less than one minute. Thus, the concentration of blood platelets and coagulation proteins are increased and results in the composition having an increased ability to accelerate and maintain blood clots. The propylene glycol in the composition is a humectant and helps impart upon the composition a hydrophilic matrix that provides increased and accelerated absorption through the various layers.

The formulation of the composition itself presented a problem in providing a suitable liquid carrier to deliver the clay to a wound that would not itself cause the clay to swell thereby negating its hemostatic properties of absorption prior to application.

The composition formulation of the present invention has successfully addressed and solved this difficulty by preparing a stable viscous liquid carrier composition that will deliver the clay to a wound site without causing the clay to reduce its water absorption capacity. The percentage of water in the formulation used to promote the dispersal of the suspension agent is offset many times over by the benefits of the addition of the humectant, propylene glycol. Thus an optimal water percentage of less than about 10% is relatively small, yet does not affect the stability of the composition.

It is further contemplated that the composition of the present invention would be efficacious in assisting clotting in both extrinsic and intrinsic sites. A ballistic wound may create more than one bleeding source in the same wound track in need of clotting. There may be a visual wound at the point of entry and an internal wound not readily visible. The body will attempt to clot an internal wound through intrinsic blood clotting mechanisms. The composition of the present invention will simultaneously assist the clotting in each of the external and internal wounds. The ability to assist in clotting multiple wounds from a single administered site is important as indirect wound tracks are most often difficult to access using current technology and treatment procedures. Furthermore, the assist in clotting using the composition of the present invention will occur with or without an exit wound being present at the hemorrhage site or sites to which the composition has traveled.

The composition has an increased elasticity that allows it to conform to a particular shape at a wound site. In addition, due to this elasticity factor, the clot remains stable and will not rupture.

Although the composition has an elevated viscosity, it has been observed that the viscosity and adhesion qualities of the composition do not hinder subsequent removal after a blood clot has formed. The composition may be removed as desired by conventional wound irrigation techniques. These wound irrigation techniques are sufficient to remove the composition once it is observed that blood flow has substantially decreased and or/stopped.

In one embodiment, the composition may absorb up to twenty four times its weight in water. The absorption is noteworthy because the composition already contains water. The composition is able to absorb, in one embodiment, up to twenty four times its weight in water, and in a preferred embodiment, up to eight times its weight in water in less than about one minute, even though the composition as provided may comprise up to about ten percent water. This becomes imperative in cases of major arterial bleeding, especially in hot or dry climates when a wound is being treated, as a patient may often be in need of hydration. Conventional treatment procedures and protocols do not provide for the administration of fluids to patients with major arterial bleeding.

The composition of the present invention not only provides rapid and critical assistance in the blood clotting process, but allows for the administration of fluids, which may also be critical to the survival of a patient while not interrupting or disturbing the therapeutic effect of the administered composition. Under many conventional medical protocols and procedures, patients with traumatic wounds do not receive fluids until they reach the operating theatre for fear that the accompanying elevated blood pressure will cause rebleeding.

The present composition has demonstrated the proper adhesive strength such that it remains in contact with tissue at and/or near a wound site in spite of a buildup of hydrostatic pressure from bleeding. This adhesion affords the composition sufficient contact time to promote clotting, even in cases of major arterial bleeding. This adhesive property provides an additional benefit in that using the composition of the present invention does not require pressure to be applied in order to facilitate a blood clot.

In one embodiment, the composition of the present invention is contained within a syringe or ejection device. The syringe may be used to apply the composition directly to a wound. Alternatively, the syringe may further have a catheter, tubing or other directional means affixed thereto for directing the application of the composition to a wound.

The syringe or ejection delivery offers many advantages. A syringe may deliver the composition through a narrow opening. Even if one cannot see the actual hemorrhage site, the composition may be introduced through an opening believed to be close to a hemorrhage site. The hemorrhage is internal and an entry point in the skin from an object, such as a bullet, shrapnel and the like, may be used to administer the composition. Thus, treatment may occur even if the hemorrhage site cannot be seen. The composition will travel internally to a hemorrhage site. There is no need to evacuate blood from a wound and, in using a syringe, there is no need to enlarge a wound site causing additional trauma in order to administer the composition.

In using a syringe to deliver the composition, a patient may be able to self-administer the composition. The composition may also be administered holding the syringe in one hand. The single handed administration may be important in self administration. Many current protocols and procedures require wound enlargement, blood evacuation, and application by more than one medical care giver in some cases which is not required using this delivery system. A further advantage of the syringe delivery is that it does not require any special training to administer. Most other wound treatments currently in use require extensive medical training to administer and may not be self-administrable. As stated above, the composition of the present invention also provided the advantageous feature that it does not require pressure be applied in order to facilitate a clot.

In another embodiment, the composition may be incorporated into a patch. Typically, patch delivered therapeutic compositions are contained within the patch by a film of polyvinyl alcohol (PVA). The PVA film dissolves when in contact with water or liquid thus dispensing the active ingredient contained therein. The composition of the present invention is formulated in an aqueous carrier for delivering the hectorite clay to a wound site. It is typically not desirable to utilize aqueous systems in patch delivery where PVA films are used. However, the propylene glycol of the present composition is a humectant and the present composition formulation has demonstrated that the small percentage of water in the formulation is bound to it and will not leach out while in contact with the PVA to prematurely dissolve the film. PVA is additionally advantageous because, in the area not immediately proximate to the hemorrhage site, PVA adheres to the surrounding tissue providing additional occlusion, aiding the retention of the hemostatic agent, and promoting increased efficacy of the hemostatic agent of the present invention.

While the invention has been described in its preferred forms or embodiments with some degree of particularity, it is understood that these descriptions have been given only by way of example and that numerous changes in the details of construction, fabrication, and use, including the combination and arrangement of parts, may be made without departing from the spirit and scope of the invention.

We claim:
1. A hemostatic agent composition comprising:
(a) 40-70% by weight of Propylene Glycol;
(b) 20-40% by weight of beneficiated Hectorite Clay;
(c) 5-15% by weight of H20;
(d) 1-10% by weight of Carbomer; and
(e) 1-10% by weight of Triethanolamine;
wherein the composition comprises a single hemostatic agent, the single hemostatic agent being beneficiated Hectorite Clay, said beneficiated Hectorite Clay having a particle size with 95% of particles being less than 76 microns, and wherein the composition facilitates blood clotting, and
wherein the composition is non-reactive relative to blood clotting proteins and blood platelets.

2. The composition of claim 1 wherein said composition absorbs a weight of liquid greater than a weight of the composition applied and used for absorption.

3. The composition of claim 1 wherein said composition absorbs up to about twenty four times the weight of liquid than a weight of the composition applied and used for absorption.

4. The composition of claim 1 wherein said composition absorbs a weight of liquid up to about eight times greater than a weight of the composition applied and used for absorption in about one minute or less.

5. The composition of claim 1 wherein the composition is non-reactive relative to the extrinsic blood clotting mechanisms.

6. The composition of claim 1 wherein the composition is non-reactive relative to the intrinsic blood clotting mechanisms.

7. The composition of claim 1 wherein the composition is applied directly to an external wound.

8. The composition of claim 1 wherein the composition is applied directly to an external wound and travels in vivo to the site of a second wound.

9. The composition of claim 1 wherein the composition is applied directly to an external wound and travels in vivo to the site of a second wound, wherein said second wound is an external wound or an internal wound.

10. The composition of claim 1 comprising:
    (a) 55.56% by weight of Propylene Glycol;
    (b) 27.78% by weight of beneficiated Hectorite Clay;
    (c) 8.34% by weight of H2O;
    (d) 4.17% by weight of Carbomer; and
    (e) 4.17% by weight of Triethanolamine;
    wherein said composition exhibits a kinematic viscosity of more than 100,00 cps.

11. A method of accelerating blood clotting of a wound comprising the steps of:
    (a) locating a wound;
    (b) providing a hemostatic agent composition; and
    (c) applying the composition into the wound:
    wherein the hemostatic agent composition comprises:
    (a) 40-70% by weight of Propylene Glycol;
    (b) 20-40% by weight of beneficiated Hectorite Clay;
    (c) 5-15% by weight of H2O;
    (d) 1-10% by weight of Carbomer; and
    (e) 1-10% by weight of Triethanolamine; and
    wherein the composition comprises a single hemostatic agent, the single hemostatic agent being beneficiated Hectorite Clay, said beneficiated Hectorite Clay having a particle size with 95% of particles being less than 76 microns, and
    wherein the composition facilitates blood clotting, and wherein the composition is non-reactive relative to blood clotting proteins and blood platelets.

12. The method of claim 11 wherein there is more than one wound source.

13. The method of claim 11 wherein there is an external wound and at least one internal wound, and further wherein the internal wound clotting is accelerated after the composition is placed into the external wound and travels in vivo to the site of the internal wound.

14. The method of claim 13 wherein the internal wound is not readily visible or locatable from the exterior of a patient.

15. The method of claim 11 wherein the providing of the composition encompasses administering up to about 250 cc of a viscous liquid composition into the wound, and wherein the viscous liquid composition is comprised of the hemostatic agent composition.

16. The method of claim 15 wherein the viscous liquid composition has a kinematic viscosity greater than 100,000 cps.

17. The method of claim 11 further comprising irrigating the application site of the hemostatic composition to remove substantially all of the hemostatic composition.

18. The method of claim 11 wherein said applying of the composition is from a syringe or ejection device.

19. The method of claim 11 wherein said applying of the composition is from a patch.

20. A hemostatic agent delivery system, comprising:
    a hemostatic agent composition; and
    a delivery assembly for permitting disposition of an amount of said hemostatic agent composition proximate a hemorrhage site;
    said delivery assembly at least temporarily retaining said amount of said hemostatic agent composition for release upon disposition proximate to the hemorrhage site; and
    wherein the hemostatic agent composition comprises:
    (a) 40-70% by weight of Propylene Glycol;
    (b) 20-40% by weight of beneficiated Hectorite Clay;
    (c) 5-15% by weight of H2O.
    (d) 1-10% by weight of Carbomer; and
    (e) 1-10% by weight of Triethanolamine; and
    wherein the hemostatic agent composition comprises a single hemostatic agent, the single hemostatic agent being beneficiated Hectorite Clay, said beneficiated Hectorite Clay having a particle size with 95% of particles being less than 76 microns, and
    wherein the hemostatic agent composition facilitates blood clotting, and
    wherein the hemostatic agent composition is non-reactive relative to blood clotting proteins and blood platelets.

21. The system according to claim 20, wherein said delivery assembly includes a support member to at least temporarily retain said amount of said hemostatic agent composition.

22. The system according to claim 20, wherein said delivery assembly includes a release member with a soluble material for dissolving and releasing said amount of said hemostatic agent composition upon disposition proximate to the hemorrhage site.

23. The system according to claim 20, wherein said delivery assembly permits disposition of said amount of said hemostatic agent composition proximate the hemorrhage site by one hand of a user.

24. The system according to claim 23, wherein said delivery assembly permits disposition of said amount of said hemostatic agent composition proximate the hemorrhage site by one hand of a user by administration of said hemostatic agent composition in a syringe or ejection device, or with a patch containing the hemostatic agent composition.

25. The system according to claim 22, wherein said release member dissolves at the hemorrhage site.

* * * * *